United States Patent
Cane'

(10) Patent No.: US 9,289,549 B2
(45) Date of Patent: Mar. 22, 2016

(54) TANK FOR DRUG INFUSION DEVICE

(71) Applicant: Cane' S.p.A., Rivoli (TO) (IT)

(72) Inventor: Mario Cane', Collegno (TO) (IT)

(73) Assignee: Cane' S.p.A., Rivoli (TO) (IT)

( * ) Notice: Subject to any disclaimer, the term of this patent is extended or adjusted under 35 U.S.C. 154(b) by 0 days.

(21) Appl. No.: 14/296,905

(22) Filed: Jun. 5, 2014

(65) Prior Publication Data

US 2014/0361048 A1     Dec. 11, 2014

(30) Foreign Application Priority Data

Jun. 6, 2013 (IT) .............................. TO2013A0467

(51) Int. Cl.
*A61M 5/145* (2006.01)
*A61M 39/12* (2006.01)
*A61M 39/10* (2006.01)

(52) U.S. Cl.
CPC .............. *A61M 5/145* (2013.01); *A61M 5/1452* (2013.01); *A61M 5/1456* (2013.01); *A61M 39/12* (2013.01); *A61M 2005/14573* (2013.01); *A61M 2039/1077* (2013.01)

(58) Field of Classification Search
USPC ........................... 222/386, 325, 326, 378, 327
See application file for complete search history.

(56) References Cited

U.S. PATENT DOCUMENTS

| | | | | |
|---|---|---|---|---|
| 1,397,510 A | * | 11/1921 | Grassi ......................... | 425/376.1 |
| 2,123,712 A | * | 7/1938 | Clark .............................. | 222/80 |
| 2,361,126 A | * | 10/1944 | Klein ............................ | 222/340 |
| 2,627,270 A | | 2/1953 | Glass | |
| 2,701,912 A | * | 2/1955 | Campbell et al. ............. | 425/172 |
| 2,702,547 A | | 2/1955 | Glass | |
| 3,353,718 A | | 11/1967 | McLay | |
| 3,392,883 A | * | 7/1968 | Roberts ........................... | 222/86 |
| 4,664,299 A | * | 5/1987 | Goncalves ..................... | 222/327 |
| 5,193,907 A | * | 3/1993 | Faccioli et al. ............... | 366/130 |
| 6,268,000 B1 | * | 7/2001 | Romer .......................... | 426/115 |
| 7,308,993 B2 | * | 12/2007 | Mineau ......................... | 222/182 |
| 7,500,584 B2 | * | 3/2009 | Schutz ........................ | 222/464.5 |
| 8,011,538 B2 | * | 9/2011 | Herman et al. ............... | 222/326 |
| 2009/0277970 A1 | * | 11/2009 | Lind et al. ......................... | 239/3 |
| 2010/0264172 A1 | * | 10/2010 | Nossbaum et al. ........... | 222/390 |
| 2011/0030845 A1 | | 2/2011 | Chong et al. | |
| 2012/0097712 A1 | * | 4/2012 | Esteve et al. .................. | 222/390 |
| 2012/0143133 A1 | | 6/2012 | Cane' | |

FOREIGN PATENT DOCUMENTS

| | | |
|---|---|---|
| EP | 0398394 B1 | 10/1993 |
| EP | 2394682 A1 | 12/2011 |
| GB | 2463051 B | 6/2012 |

OTHER PUBLICATIONS

Search Report and Written Opinion issued for counterpart Italian Patent Application No. TO2013A000467 dated Feb. 2014.
Search Report and Written Opinion dated Oct. 1, 2014 issued for counterpart European Patent Application No. 14171196.

* cited by examiner

*Primary Examiner* — Donnell Long
(74) *Attorney, Agent, or Firm* — Howson & Howson LLP

(57) ABSTRACT

Tank (11) for a drug infusion device (41), comprising a hollow cylindrical body (13) provided at its front with an opening (15) for the passage of the drug and in its inside with a plunger (25) slidable within the tank for drawing in and/or injecting the drug through said opening, said tank being provided at its rear with a coupling part for ensuring the mechanical connection of the tank (11) with a complementary coupling part provided in the infusion device (41), said coupling parts defining together a bayonet-like connection coupling, said coupling part of the tank (11) being housed inside the cylindrical body (13).

10 Claims, 10 Drawing Sheets

TANK FOR DRUG INFUSION DEVICE

TECHNICAL SECTOR

The present invention concerns a tank for a drug infusion device.

PRIOR ART

In the art drug infusion devices, also referred to as "infusion pumps", are known, these being able to supply the drug contained in liquid form inside a tank over a long period of time lasting even many hours or days.

These devices may be mainly of the mechanical or electro-mechanical type and comprise an electric motor and a series of gears and mechanical components which are housed inside a container from which an extendable rod protrudes. The container is designed to receive an interchangeable tank, for example a disposable syringe or a phial or the like. The extendable rod gradually presses, by means of a pusher provided at the end of the rod, against a plunger sliding inside the tank, causing at the same time discharging of the drug from the tank through an opening provided for this purpose.

An example of a drug infusion device of the aforementioned type is described in EP 2,394,682.

In some applications the drug infusion devices use tanks prefilled with a drug and designed for this purpose; in other cases it is possible to use tanks in the form of disposable syringes of the standard type which are also marketed for other uses, or are very similar to those of the standard type, but are made by the manufacturer of the infusion device. Standard syringes, as is known, have at the open base radial lugs forming a support for the user's fingers during infusion or manual drawing-in of the drug. In the known infusion devices, in particular in devices of the portable type, the aforementioned lugs are used to stably fix the syringe in the device. A ferrule provided on the top end of the device is provided for this purpose with diametrically opposite and coplanar radial grooves between which an axial inlet is provided for positioning the lugs of the syringe against the base of the ferrule. Rotation of the syringe about its longitudinal axis, generally through about 90°, causes engagement of the syringe lugs inside the corresponding grooves in the pump ferrule.

This system of locking the syringe on the pump, which makes use of the presence of the radial lugs provided on the base of the syringe, results however in a considerable radial volume compared to the working cross-section of the tank defined in the syringe. For example the radial volume of a standard syringe at the base where the radial lugs are provided is substantially bigger than the working cross-section of the tank defined therein, owing to the presence of the lugs.

Since they are drug infusion devices intended to be worn and carried by the patient, for example hung around the neck by means of a strap or fixed to the waist by means of a belt, it is evident that these devices must have dimensions which are as small as possible.

The presence of a syringe with excessively large dimensions furthermore conflicts with efforts made by the manufacturers of infusion devices to produce pumps which are increasingly more compact in order to favor the portability thereof. On the other hand a small-size syringe is not always compatible with the therapy in progress and moreover results in the need for frequent replacement, with consequent drawbacks for the patient.

For some pathologies a large quantity of drug is required and may be transferred to the patient using a single pump connected to several infusion sites by means of Y connectors or the like. Nowadays therefore it is not uncommon for there to be the need for a single tank with a capacity of even more than 50 cc or even more than 100 cc. In such cases, the use of radial lugs significantly hinders the possibility of wearing the device since the diameter of the syringe in the region of the lugs would be significantly greater than the volume of the infusion pump. For the same capacity, the use of longer syringes in order to reduce their cross-section is equally impossible since it would require a corresponding increase in the pump length, the pump having to have an extendable rod suitable for the length of the plunger stroke inside the syringe.

A further drawback of the locking system which makes use of the radial lugs of the syringe consists in the fact that the lugs tend to flex under the thrust of the pusher when it presses against the syringe plunger during infusion of the drug. This tendency to flex is all the greater the greater the resistance to dispensing of the drug. In extreme cases the syringe may therefore risk being pushed out of the seat provided in the device, with even severe consequences for the patient owing to interruption of the therapy.

A first object of the invention is therefore to provide a tank for a drug infusion device, which has a small volume widthwise and which may be locked on the infusion device in a stable and reliable manner.

A further object of the invention is to provide a tank of the aforementioned type which may be made with any dimensions, in particular large dimensions, for example with a capacity of more than 50 cc.

Last but not least an object of the invention is to provide a tank for a drug infusion device which can be made at a low cost and is therefore suitable for being produced industrially on a large scale.

DESCRIPTION OF THE INVENTION

These and other objects are obtained with the tank for a drug infusion device as claimed in the attached claims.

Advantageously, owing to the provision of a rear coupling part housed inside the tank, the radial lugs may be avoided, thus limiting the width of the tank substantially to the working cross-section for containing the drug.

A further advantage of the invention consists in the fact that a radial-tooth bayonet coupling, provided between the tank and the ferrule of the infusion device, ensures stable and effective locking of the two components, avoiding the risk of tank becoming detached, even in the presence of high thrusting forces acting against the sliding plunger.

As a result of this coupling system it is moreover possible to connect the tank to the infusion device at a predetermined fixed axial distance, something which would not be possible for example in the case of an internal screw-type coupling.

One advantage of the invention is also due to the provision, in one particular embodiment, of an opening for the drug which is oriented perpendicularly with respect to the longitudinal axis of the syringe, thus helping reduce the overall length of the tank.

A further advantage of the invention consists in the fact that the coupling part provided on the infusion device may be incorporated in a substantially circular ferrule which is easily adapted to an infusion pump, in particular of the portable type.

Last but not least an advantage of the invention consists in the possibility of manufacturing the tank by means of conventional plastic-molding techniques, using the wall itself of the tank for incorporation of the coupling part provided therein.

BRIEF DESCRIPTION OF THE FIGURES

A number of preferred embodiments of the invention will be provided by way of a non-limiting example with reference to the accompanying drawings in which.

DESCRIPTION OF A PREFERRED EMBODIMENT

Figure 1:
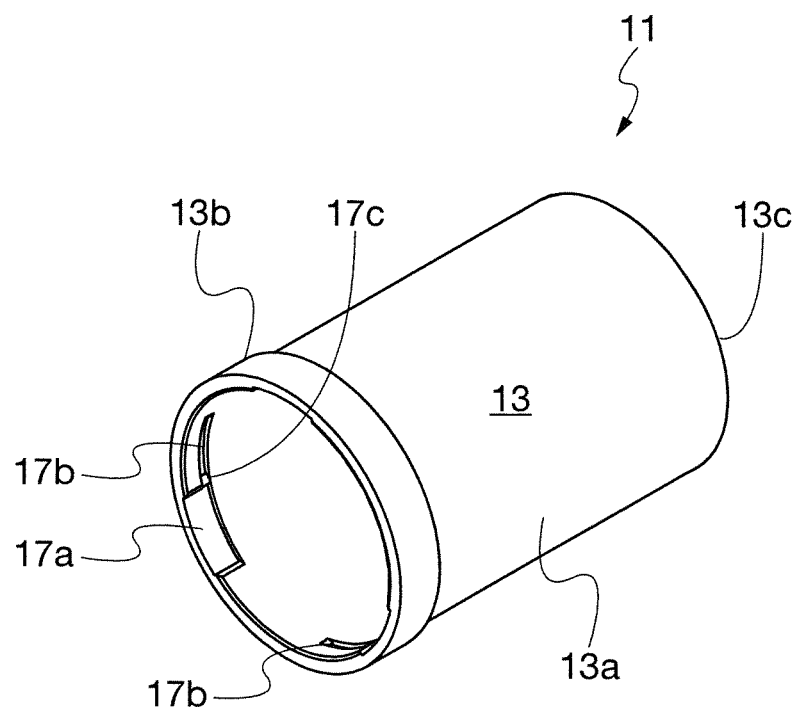
FIG. 1 is a rear perspective view of a first embodiment of the tank.
Figure 2:
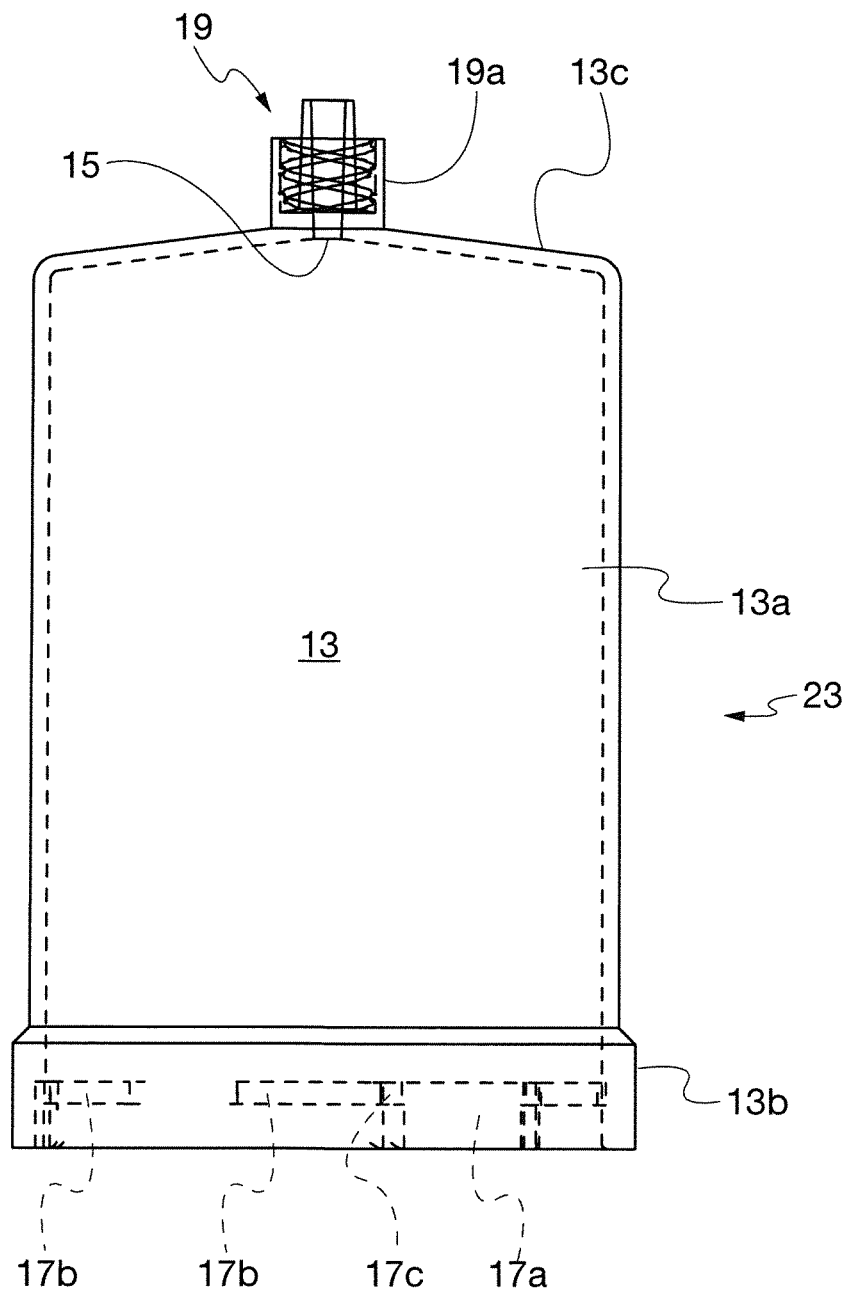
FIG. 2 is a cross-sectional view along a longitudinal plane of the tank according to FIG. 1.

With reference to FIGS. 1 and 2, a tank 11 for a drug infusion device is shown, said tank comprising a hollow cylindrical body 13 provided with a side wall 13a and at the front with an opening 15 for passage of the liquid contained therein to and/or from the tank 11. The body 13 may be advantageously made using plastic-molding techniques, similar to that which occurs in the sector for the production of disposable syringes for medical use.

According to the invention and as will become clearer from the description below, the body 13 is designed to be connected at the rear stably and rapidly to a drug infusion device by means of a connection coupling consisting of two parts, the part associated with the body 13 being advantageously housed at the rear inside the tank 11.

According to the invention, said connection coupling comprises a bayonet-type coupling which, as is known, is a system for quick-locking a part which must be frequently removed and is characterized by a two-stage operation: axial displacement and subsequent rotation of the two parts to be connected to each other.

According to a preferred embodiment of the invention the connection coupling is of the radial-tooth type and, in the example shown, comprises a female part provided with three axial inlets 17a at 120° which are formed in the wall 13a of the body 13 at the base of said body 13. Said axial inlets 17a are radially open towards the inside of the tank 11 and communicate with a corresponding number of grooves 17b which extend circumferentially between one axial inlet 17a and another and have an interruption at the end opposite to the respective inlet 17a so as to form an abutment for the teeth of the male part of the connection coupling. The grooves 17b all extend in a clockwise or anticlockwise direction, depending on the preferred direction of rotation which is to be assigned to the coupling for establishing the connection between the two parts. Said grooves 17b are also preferably arranged coplanar in a plane substantially perpendicular to the longitudinal axis of the cylindrical body 13 of the tank 11. Radial reliefs 17c are preferably provided between the inlets 17a and the respective grooves 17b so as to form a corresponding non-return abutment for the male part of the coupling, which prevents accidental disengagement of the bayonet coupling.

Still with reference to the embodiment shown, the axial inlets 17a and the corresponding grooves 17b communicating with them are formed in the wall 13a of the body 13 of the tank 11, in a base portion 13b having a thickness greater than—for example about twice—the thickness of the remaining wall 13a of the cylindrical body 13. In one example of embodiment of a tank with 100 cc capacity, the wall 13a of the cylindrical body 13 had a thickness of about 1.5 mm, and the thickened portions 13b, in which the inlets 17a and the grooves 17b are formed, had a thickness of about 3.0 mm.

In the example shown, the opening 15 for the drug is formed in a front end 13c of the cylindrical body 13, substantially in the centre and concentric with the central longitudinal axis of the cylindrical body 13. Said end 13e forms moreover the front base of the body 13 and is preferably tapered towards the opening 15 so as to allow all the liquid to flow out from the tank at the end of the plunger stroke against said front base. At said opening 15 there is further provided a spout 19 provided with a connecting joint 19a, for example of the "Luer lock" type, as in the example shown. The connector 19 allows a cannula or a needle or other medical device to be combined, for passage of the drug. However, it is also possible to envisage positioning the opening 15 in a different manner, for example radially on the side wall 13a of the cylindrical body 13, and moreover other types of connecting joints, different from the Luer lock, may be provided.

Figure 3:
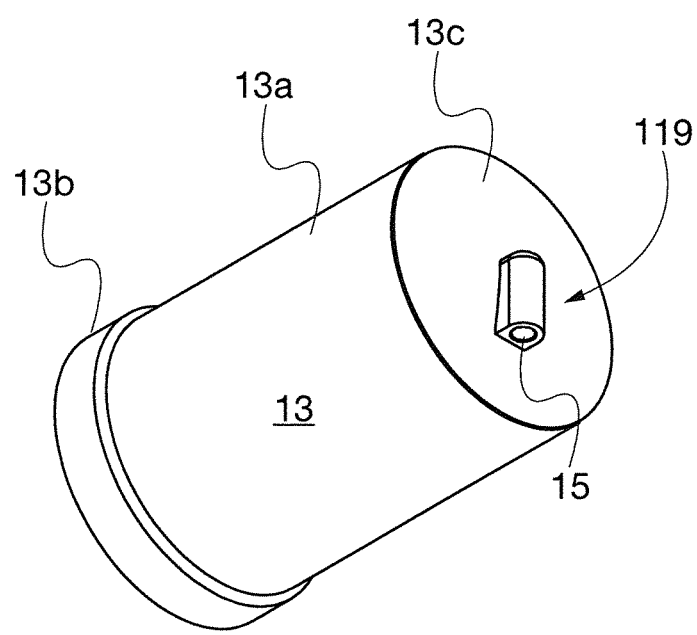
FIG. 3 is a front perspective view of a second embodiment of the tank.

With reference to FIG. 3 this shows the tank 11 in a second embodiment of the invention provided with an opening 15 for the drug and corresponding spout 119 which are oriented radially on the front base 13c of the tank 11. According to this embodiment of the invention it is envisaged that the tank 11 is provided with an opening 15 for the drug oriented perpendicularly with respect to the longitudinal axis of the cylindrical body 13 instead of being parallel as in the first embodiment. Owing to this arrangement the length of the tank 11 is advantageously smaller than in the case where the opening 15 is oriented axially and consequently also the overall length of the infusion device, complete with tank, will be smaller, to the advantage of the portability of the device itself during infusion.

Figure 4:
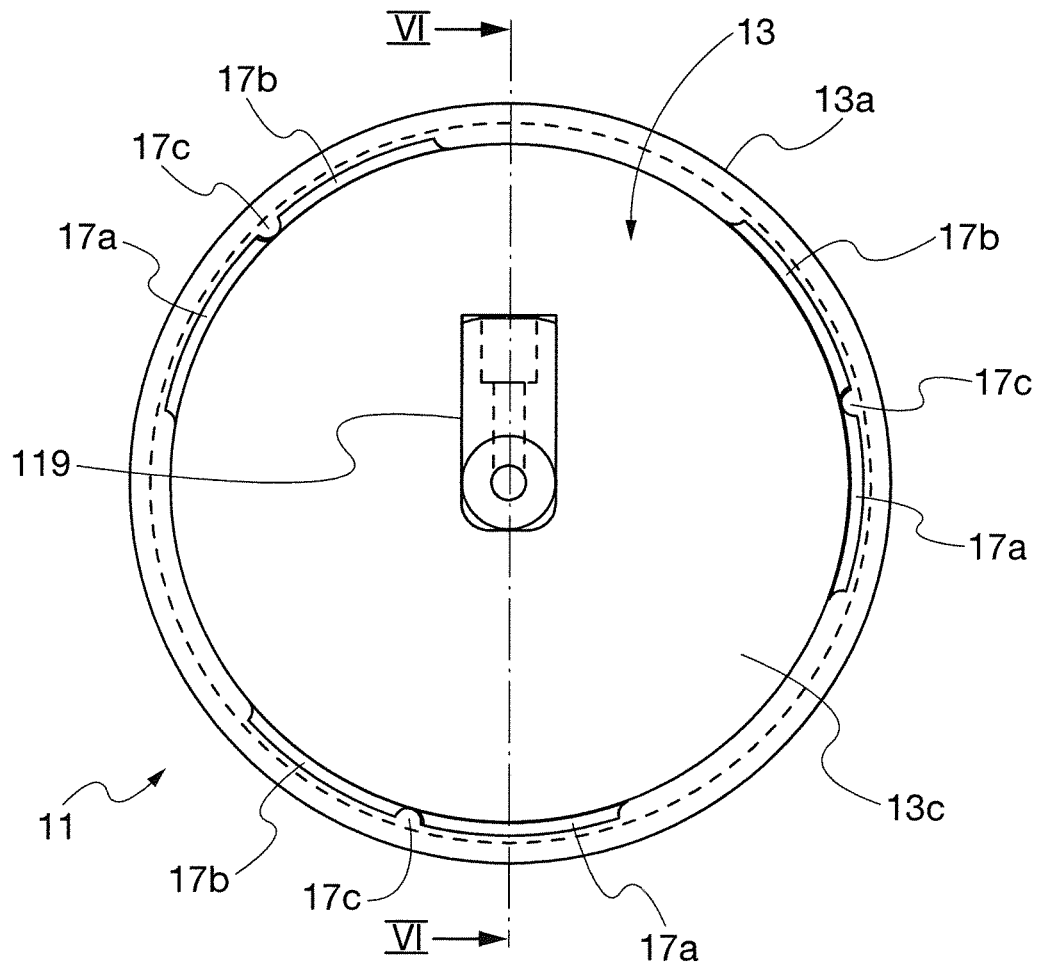
FIG. 4 is a transparent perspective view of the tank shown in FIG. 3.
Figure 5:
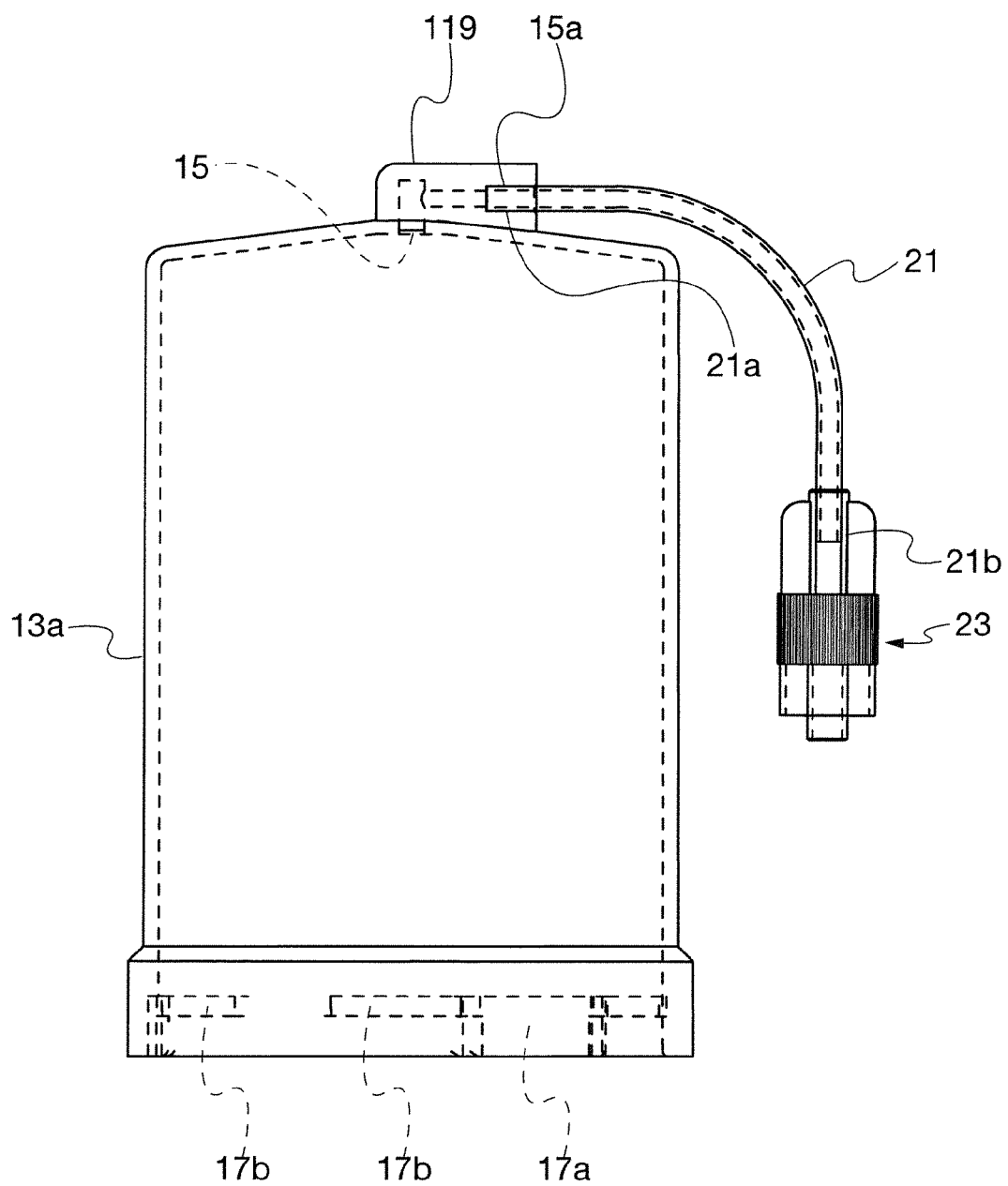
FIG. 5 is a transparent side view of the tank shown in FIG. 4 provided with a cannula.

As can be seen more clearly in FIGS. 4 and 5, moreover, the opening 15 for the drug may comprise a first portion 15a directed outwards and having a cross-section sufficient for receiving a corresponding end portion 21a of a pipe 21 which is preferably flexible and may be attached stably thereto for example by means of gluing with suitable adhesive. In this way, the connector 23, for example of the Luer lock type as in the example shown, for connecting a drug discharge cannula or any other device, may be associated with the free end 21b of the pipe 21, opposite to that 21a fixed to the tank 11 in the region of the spout 119. This arrangement advantageously allows the axial volume of the assembly to be limited compared to the case where the connector 23 is arranged axially, also resulting in greater flexibility of use, owing to the possibility of orienting the connector 23 as required.

Figure 6:
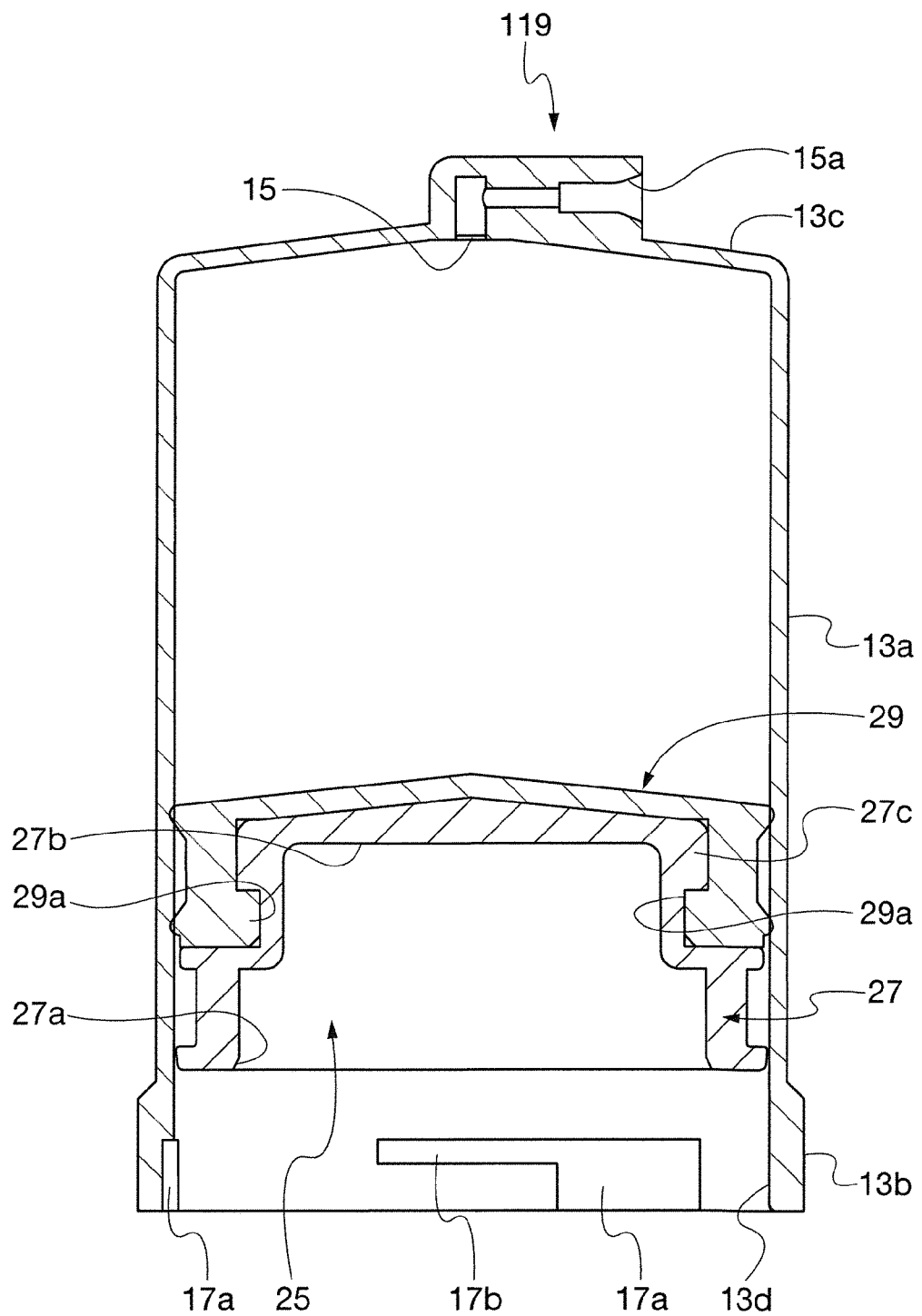
FIG. 6 is a cross-sectional view along the line VI-VI of FIG. 4.

With reference now to FIG. 6 this shows the plunger 25 provided in the tank 11 and having mainly the function of allowing evacuation of the liquid contained inside the tank through the opening 15, but also being able to be used for drawing in the liquid inside the tank through said opening 15. In general, drawing-in of the liquid will be performed by means of a rod (not shown) which is connected to the plunger 25 removably and by means of which the plunger 25 may be brought towards the open base 13d of the tank 11. Once the liquid has been drawn in, it will therefore be possible to remove the rod, separating it from the plunger 25 in order to prepare the tank 11 for connection to an infusion device by means of the bayonet connection coupling. Small-size tanks, typically with a capacity of up to 50 cc, may be filled in the manner described, namely by making use of the sliding action of the plunger 25 which is positioned manually towards the base 13d of the tank by means of the rod. In other situations, in particular in the case of larger-size tanks, typically with a capacity of more than 50 cc, the force required for filling would be excessive and it is therefore preferable to inject the liquid inside the tank through the opening 15 provided at the front end 13c of the tank 11, for example making use of a syringe, previously filled with the liquid to be injected inside the tank 11. In this case the pressure of the liquid which enters into the tank under the thrust of the plunger of the prefilled syringe causes retraction of the plunger 25 towards the base 13d of the tank 11, as the liquid penetrates inside it.

In the example shown, the plunger 25 comprises a hollow rigid body 27, for example made of plastic, with a cylindrical form and with an open base 27a for entry of the pusher of the infusion device and provided with a front base 27b for seating said pusher. Still with reference to the example of embodiment shown, the cylindrical body 27 is fitted with a sealing gasket made of rubber or the like, in the form of a cap or hood 29, which partially surrounds the side wall 27c of the rigid body 27 and engages with a terminal flap 29a inside a groove 27d formed circumferentially in the body 27 and which covers completely the closed base 27b of the body 27. The cap or hood 29 creates the necessary hydraulic seal against the inner surface of the side wall 13b of the body 13 of the tank 11.

It should be noted that, in order to ensure that practically all the liquid contained inside the tank 11 is evacuated when the plunger 25 is positioned at the end of its stroke against the front end 13c of the tank 11, the outlet opening 15 must be positioned conveniently on the front base 13c tapered towards said opening 15, as in the example shown.

Figure 7:
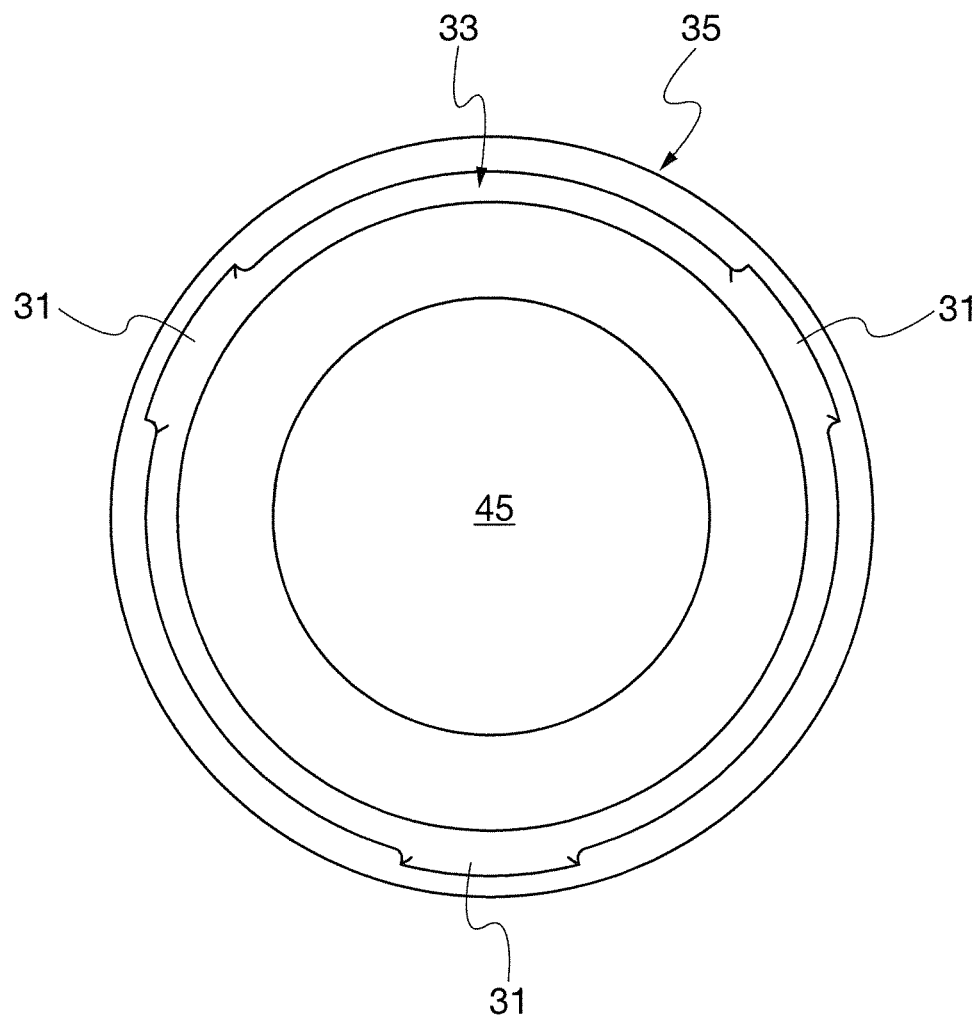
FIG. 7 is a top plan view of the infusion device complete with pusher.

With reference to FIG. 7, the three radial inlets 17a of the female coupling part provided in the tank 11 are intended to receive a corresponding number of radial teeth 31 arranged at 120° and projecting on the outside of a cylindrical collar 33 which projects axially from a ferrule 35 fixed onto the infusion device and provided, for example in the centre as in the example shown, with a hole for the passage of the extendable rod on which there is fixed the pusher 45 which presses against the plunger 25 of the tank 11 during infusion.

According to the invention, the inlets 17a, the grooves 17b and correspondingly the teeth 31 may also consist of a number other than three, for example two or four or more.

Engagement of the tank 11 on the ferrule 35 is performed by inserting the teeth 31 inside the inlets 17a and rotating the tank 11 rotated on the ferrule 35 until the teeth 31 are positioned beyond the radial reliefs 17c, where provided. Advantageously, the snap action which occurs when the teeth 31 pass beyond the reliefs 17c at the end of the rotational movement of the tank 11 with respect to the ferrule 35 also produces a locking effect which can be felt and heard, thus reassuring the user.

The base 35a of the ferrule 35 may be advantageously made with a circular form, as in the example shown, or with different forms depending on the needs and the form of the device with which it must be associated.

Figure 8:
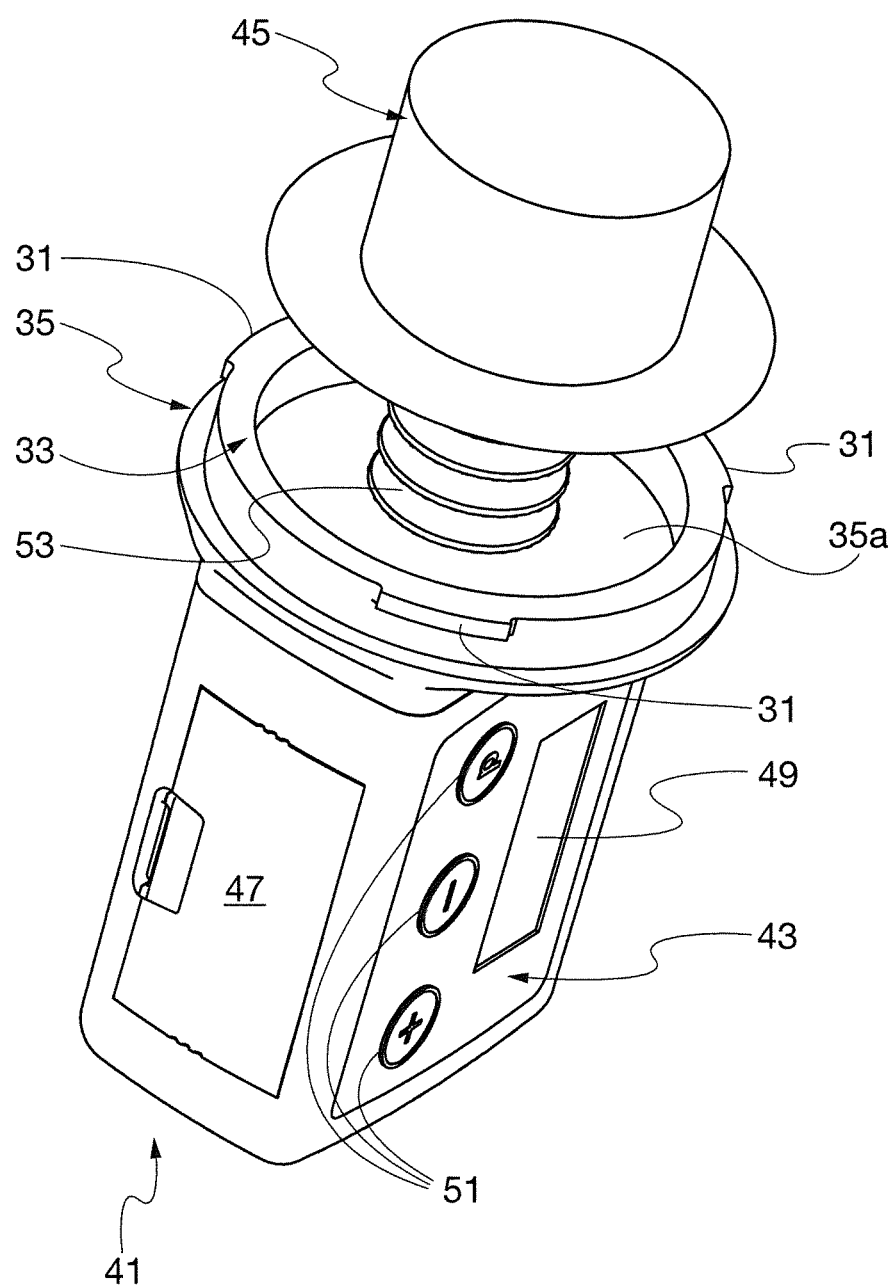
FIG. 8 is a front perspective view of the infusion device shown in FIG. 7 with the pusher partially extended.

With reference to FIG. 8, this shows an infusion device 41 of the electromechanical type provided with an electric motor and with mechanical components which are located inside a container 43 and which cause the axial movement of a longitudinal rod which protrudes from the device 41 passing through the ferrule 35 and terminates in a pusher 45. The device 41 shown is moreover of the portable type and has a housing closed by an access flap 47 for the batteries, a display 49 and buttons 51 for controlling the various functions. The rod part which protrudes from the device 41 is preferably surrounded by an extendable protection bellows 53 which prevents the entry of dust and liquid.

Figure 9:
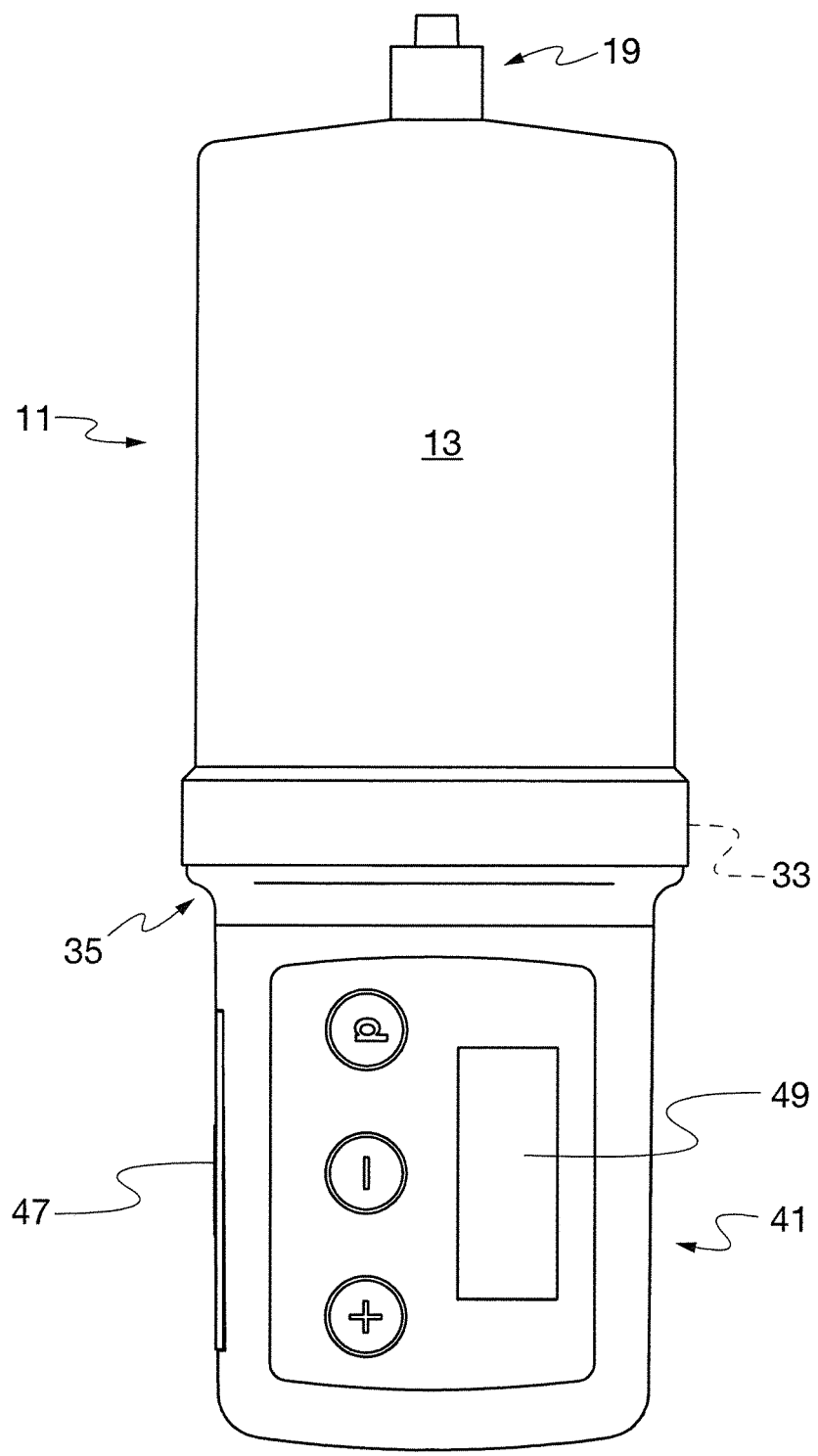
FIG. 9 is a side view of the infusion device shown in FIG. 7 with which a tank according to the first embodiment is associated.

As can be seen more clearly in FIG. 9, with reference to the device 41 shown the ferrule 35 performs the function of a lid for one of the bases of the infusion device 41 and also has the outer edge of the collar 33 which projects radially outwards with respect to the lateral volume of the device 41 and which allows stable gripping by the user, in particular during the operations for locking and disengaging the tank 11 to/from the device 41. It can be noted that in the example shown the tank 11 associated with the device 41 is provided with a spout 19 of the axial type purely by way of example and that said spout may also be of the radial type 119 or any other kind.

Figure 10:
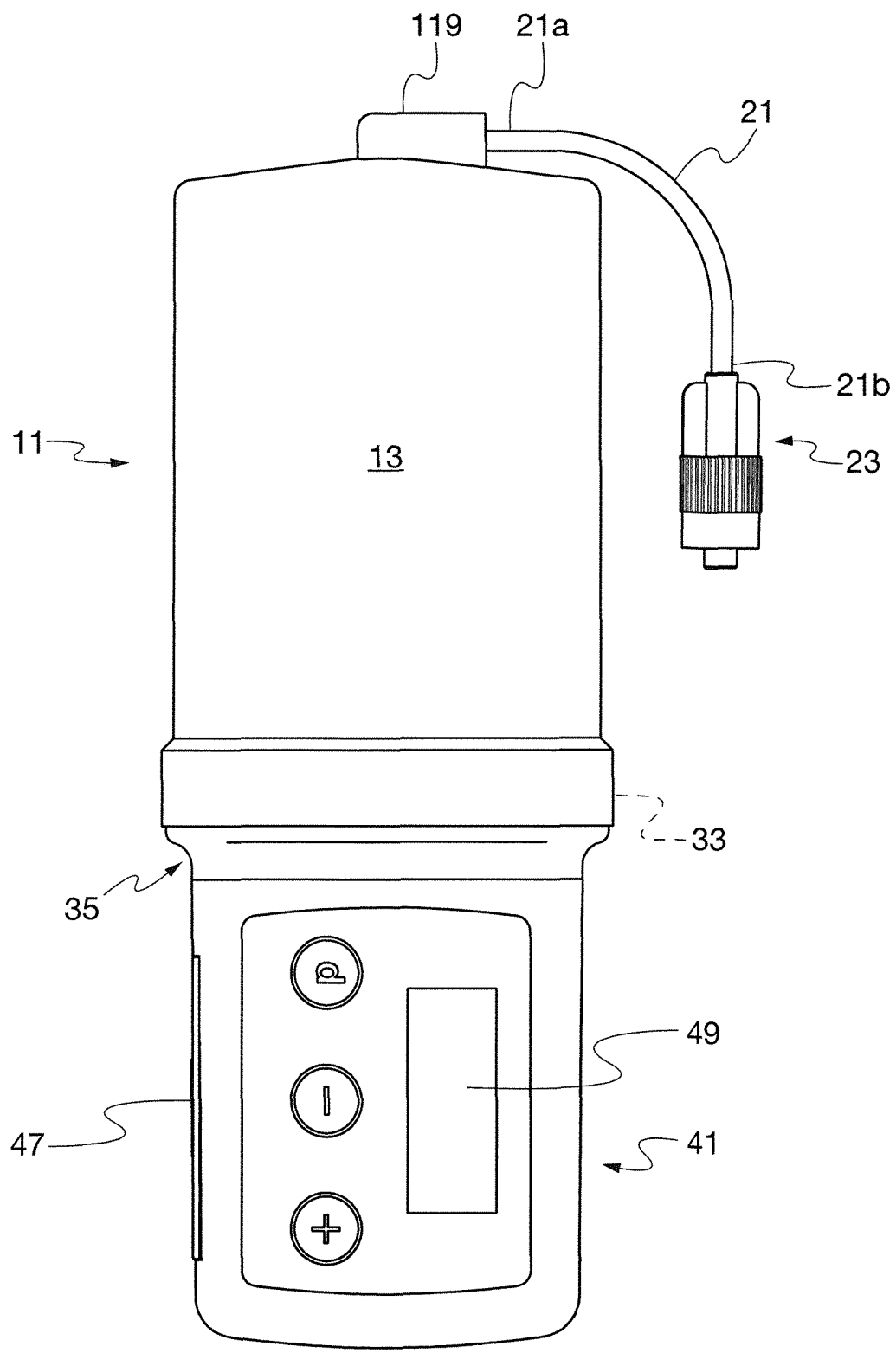
FIG. 10 is a view similar to that of FIG. 9 where a tank according to the second embodiment is associated with the infusion device.

With reference to FIG. 10 this shows the infusion device 41 associated with a tank 11 designed in accordance with the second embodiment of the invention, namely with a spout 119 for the drug arranged at right angles to the axis of the cylindrical body 13. Moreover, the tank 11 is provided with a pipe 21 stably associated with the opening 15 and in turn having on its free end 21b a coupling of the Luer lock type 23. The configuration shown is the preferred arrangement according to the invention since it is able to achieve the minimum volume widthwise, owing to the bayonet coupling which is contained inside the tank 11 and the outlet 15 oriented at right angles and provided with an external Luer lock coupling at the front end of a flexible pipe portion; for these reasons it also possible to achieve the minimum volume lengthwise.

Figure 11:
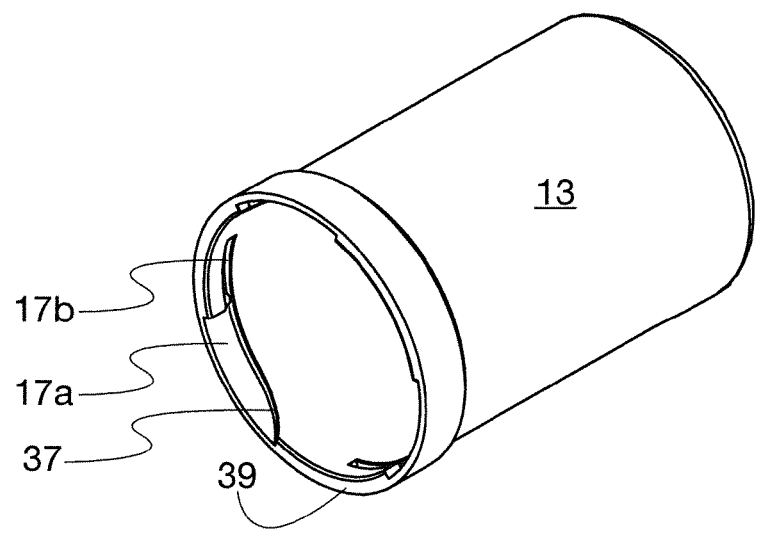
FIG. 11 is a rear perspective view of a variation of embodiment of the coupling part of the tank.
Figure 12:
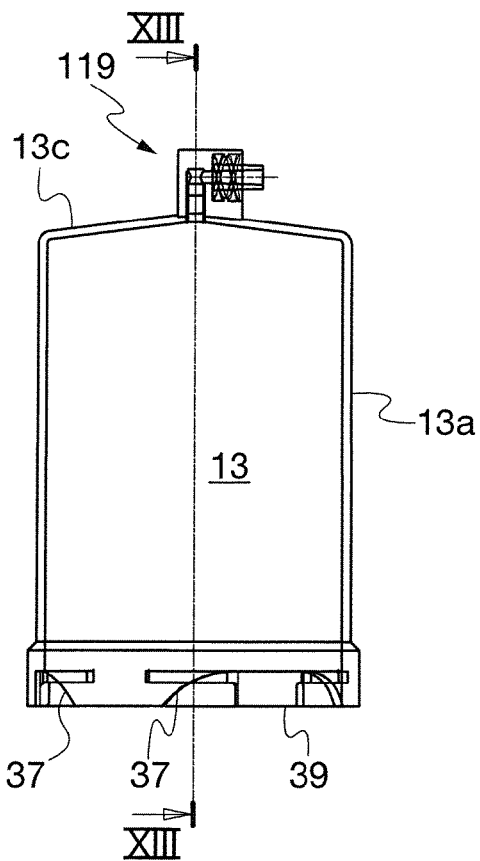
FIG. 12 is a cross-sectional view along a longitudinal plane of the tank shown in FIG. 11.
Figure 13:
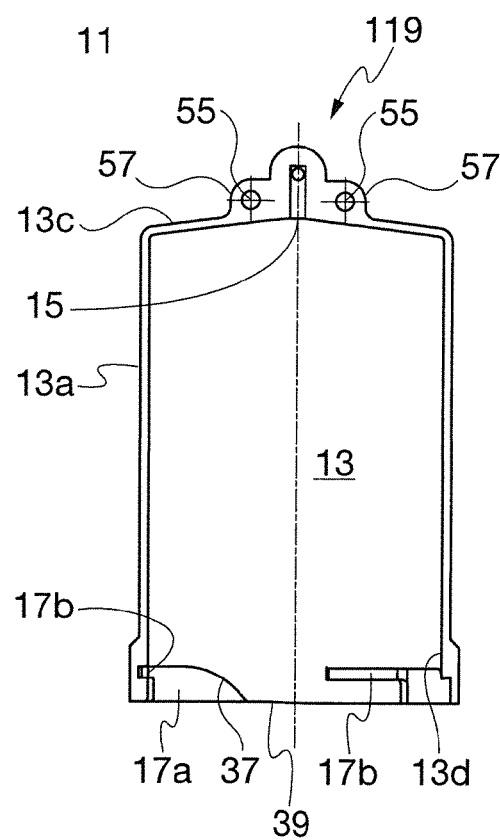
FIG. 13 is a cross-sectional view along the line XIII-XIII of FIG. 12.

With reference to FIGS. 11 to 13, these show a variation of embodiment of the coupling part of the tank 13 according to the invention. According to this variant, the axial inlets 17a of the female coupling part comprise a rear zone, opposite to the grooves 17b, which extends so as to form a circle arc 37 connected with the edge 39 to the base of the tank 13. This arrangement is advantageous, in particular when the tank 13 is removed from the device 41. In order to remove the tank 13 from the device 41 it is in fact necessary to rotate initially the tank 13 with respect to the ferrule 35. In the embodiments described hitherto, the rear zone of the axial inlets 17a is square-shaped and therefore forms an abutment for stopping rotation of the tank 13. In accordance with this variation of embodiment, instead, when the tank 13 is rotated so as to separate it from the infusion device 41, the rear circle-arc zone 37 gradually interferes with the radial teeth 31. The gradual interference between the teeth 31 and the arched zone 37 produces a corresponding thrust which is correspondingly gradual in the axial direction, thereby moving the tank 13 away from the ferrule 35. As a result of this configuration of the female coupling part it is possible overcome, without any force on the part of the user, the resistance produced by the engagement between the pusher 45 and the plunger 25. The engagement between the pusher 45 and the plunger 25 is achieved, for example, by the presence of means able to prevent the free sliding movement of the plunger 25 inside the body of the tank 13. As is known, the free sliding movement of the plunger 25 could result in an undesirable free flow effect. These means are known and may consist of ratchet systems, knurling, or the like.

Still with reference to FIGS. 11 and 12 it can be seen that the tank 13 according to the invention, even when it incorporates a spout of the radially oriented type, may be provided with a Luer lock joint incorporated in the body of the spout 119.

With reference still to FIGS. 11 and 12 these also show a particular solution to the problem of how to suspend the device 41 from a hook or the neck of a user, by means of a chain, a cord or the like. A pair of eyelets 55 is defined on a pair of lugs 57 which extend axially from the base 13c of the tank 13 to the sides of the opening 15. The lugs 57 are preferably formed integrally with the body of the tank 13. Although the invention has been described with reference to a configuration in which the female part of the connection coupling is associated with the tank 11 and the male part is associated with the ferrule 35 attached to the infusion device 41, still according to the invention it will also be possible to provide a reverse configuration for coupling together the tank 11 and the pump 41, namely one in which the female coupling part is formed in the ferrule 35 provided on the infusion device 41 and the male coupling is provided in the body 11 of the tank. The male coupling part provided in the tank 11 will be preferably formed in the wall 13a of the body 13 so as not to project radially inside the body 13 and interfere with the plunger 25, when the latter is inserted inside the tank 11 during manufacture of the tank itself.

The invention as described and illustrated may be subject to numerous variations and modifications which fall within the same inventive principle.

What is claimed:

1. A tank (11) for a drug infusion device (41), comprising a hollow cylindrical body (13) provided at its front with an opening (15) for the passage of the drug and in its inside with a plunger (25) slidable within the tank for drawing in and/or injecting the drug through said opening, said tank being provided at its rear with a coupling part for ensuring the mechanical connection of the tank (11) with a complementary coupling part provided in the infusion device (41), wherein said coupling parts define together a bayonet-like connection coupling, wherein said coupling part of the tank (11) is housed inside the cylindrical body (13), wherein the bayonet-like connection coupling is of the kind having radial teeth and comprises a female part associated with the tank and a male part associated with the infusion device, wherein the female part is associated with the tank and is provided with axial inlets (17a) formed in the wall (13a) of the cylindrical body (13) at the base of said cylindrical body (13) and radially open towards the inside of the tank (11) and communicating with a corresponding number of radial grooves (17b) circumferentially extending between one axial inlet (17a) and another and having an interruption at the end opposite to the respective inlet 17a for forming an abutment for the teeth of the male part of the bayonet-like connection coupling, and wherein radial reliefs (17c) are provided between the inlets (17a) and the respective grooves (17b) so as form a corresponding non-return abutment for the male part of the coupling, which prevents accidental disengagement of the bayonet coupling.

2. The tank as claimed in claim 1, wherein the grooves (17b) are at least two in number and all extend in a clockwise or anticlockwise direction, depending on the preferred direction of rotation to be assigned to the coupling for establishing the connection between the two parts.

3. The tank as claimed in claim 2, wherein said grooves (17b) are further arranged co-planar in a plane substantially perpendicular to the longitudinal axis of the cylindrical body (13) of the tank (11).

4. The tank as claimed in claim 1, wherein the axial inlets (17a) and the corresponding grooves (17b) communicating with them are foamed in the wall (13a) of the body (13) of the tank (11), in a base portion (13b) having a thickness greater than the thickness of the remaining wall (13a) of the cylindrical body (13).

5. The tank as claimed in claim 1, wherein at said opening (15) for the drug there is further provided a spout (19;119) oriented parallel or perpendicularly with respect to the longitudinal axis of the cylindrical body (13).

6. The tank as claimed in claim 5, wherein the opening (15) for the drug comprises a first portion (15a) directed outwards and having a cross-section sufficient for receiving a corresponding end portion (21a) of a flexible pipe (21) that is attached stably thereto by means of gluing and is provided at its free end (21b) with a connecting joint (23).

7. A drug infusion device (41) comprising a tank (11) made in accordance with claim 1, said infusion device comprising a coupling part for ensuring the mechanical connection of the device (41) with a complementary coupling part provided in said tank (11), wherein said coupling parts define together a bayonet-like connection coupling and wherein said coupling part of the device (41) is formed in a cylindrical collar (33) projecting axially from a ferrule (35) attached to the infusion device.

8. The device as claimed in claim 7, wherein said coupling part of the device (41) has radial teeth (31) projecting on the outside of the collar (33).

9. The tank according to claim 1, wherein the axial inlets (17a) of the female coupling part provided in the tank (11) are intended to receive a corresponding number of radial teeth (31) arranged at 120° and projecting on the outside of a cylindrical collar (33) which projects axially from a ferrule (35) fixed onto the infusion device (41).

10. The tank according to claim 9, wherein the axial inlets (17a) of the female coupling part comprise a rear zone, opposite to the grooves (17b), which extends so as to form a circle arc (37) connected with an edge (39) to the base of the tank (13) whereby when the tank (13) is rotated so as to separate it from the infusion device (41), the rear circle-arc zone (37) gradually interferes with the radial teeth (31) thereby producing a corresponding thrust which is correspondingly gradual in the axial direction, thereby moving the tank (13) away from the ferrule (35).

* * * * *